US00PP30531P2

(12) United States Plant Patent
Nishikawa

(10) Patent No.: US PP30,531 P2
(45) Date of Patent: May 21, 2019

(54) ***BIDENS* PLANT NAMED '15S27'**

(50) Latin Name: *Bidens triplinervia*
Varietal Denomination: 15S27

(71) Applicant: Koichiro Nishikawa, Katuta-gun (JP)

(72) Inventor: Koichiro Nishikawa, Katuta-gun (JP)

( * ) Notice: Subject to any disclaimer, the term of this patent is extended or adjusted under 35 U.S.C. 154(b) by 0 days.

(21) Appl. No.: 15/732,266

(22) Filed: Oct. 17, 2017

(51) Int. Cl.
*A01H 5/02* (2018.01)

(52) U.S. Cl.
USPC ..... Plt./410
CPC ..... *A01H 5/02* (2013.01)

(58) Field of Classification Search
USPC ..... Plt./410
CPC ..... A01H 5/02
See application file for complete search history.

(56) References Cited

PUBLICATIONS http://ehrnet.com/wordpress/wp-content/uploads/2017/6/2017-Spring-Trials-Report-web-version-6-23-17.pdf; 2017; 28 pages.*
https://conceptplants.com/varieties/bidens-beezar-fire-whee1-15-s-27/; 2018; 1 page.*

* cited by examiner

*Primary Examiner* — Kent L Bell
(74) *Attorney, Agent, or Firm* — Penny J. Aguirre

(57) ABSTRACT

A new cultivar of *Bidens* named '15S27' that is characterized by its very compact plant habit and its large inflorescenses that are red in color.

2 Drawing Sheets

Botanical classification: *Bidens triplinervia.*
Variety denomination: '15S27'.

CROSS REFERENCE TO A RELATED APPLICATION

This application is co-pending with a U.S. Plant Patent Application filed for a plant derived from the same breeding program that is entitled *Bidens* Plant Named '15S25' (U.S. Plant patent application Ser. No. 15/732,272).

BACKGROUND OF THE INVENTION

The present invention relates to a new and distinct cultivar of *Bidens triplinervia* plant, botanically of hybrid origin and known as *Bidens* '15S27' and will be referred to hereinafter by its cultivar name, '15S27'. The new cultivar of *Bidens* is an herbaceous perennial grown for landscape and container use.

'15S27' arose from crosses made by the Inventor in Quito, Equador between unnamed and unpatented proprietary plants of *Bidens triplinervia* from his breeding program. Seeds were pooled from the crosses and therefore the exact parents are unknown. '15S27' was selected in 2014 as a single unique plant amongst the resulting seedlings.

Asexual propagation of the new cultivar was first accomplished by stem cuttings under the direction of the Inventor 2014 in Quito, Equador. Asexual propagation by stem cuttings has shown that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish '15S27' as a unique cultivar of *Bidens*.

1. '15S27' exhibits a very compact plant habit.
2. '15S27' exhibits inflorescenses that are red in color.
3. '15S27' exhibits inflorescenses that are large in size.

'15S27' can be most closely compared to *Bidens* 'Florbikanre' (U.S. Plant Pat. No. 24,867) and *Bidens* '15S25'. 'Florbikano' differs from '15S27' in having a less compact plant habit and inflorescenses that are smaller in size and less red in color. '15S25' is similar to '15S27' in having a very compact plant habit. '15S25' differs from '15S27' in having orange-yellow inflorecences.

BRIEF DESCRIPTION OF THE DRAWINGS

The accompanying colored photographs illustrate the overall appearance and distinct characteristics of the new *Bidens*. The photographs were taken of a 3 month-old plant of '15S257' as grown in an unheated greenhouse in a 13-cm container in Boskoop, The Netherlands.

The photograph in FIG. 1 provides a side view of '15S27' and shows the plant habit in bloom.

Figure 1:
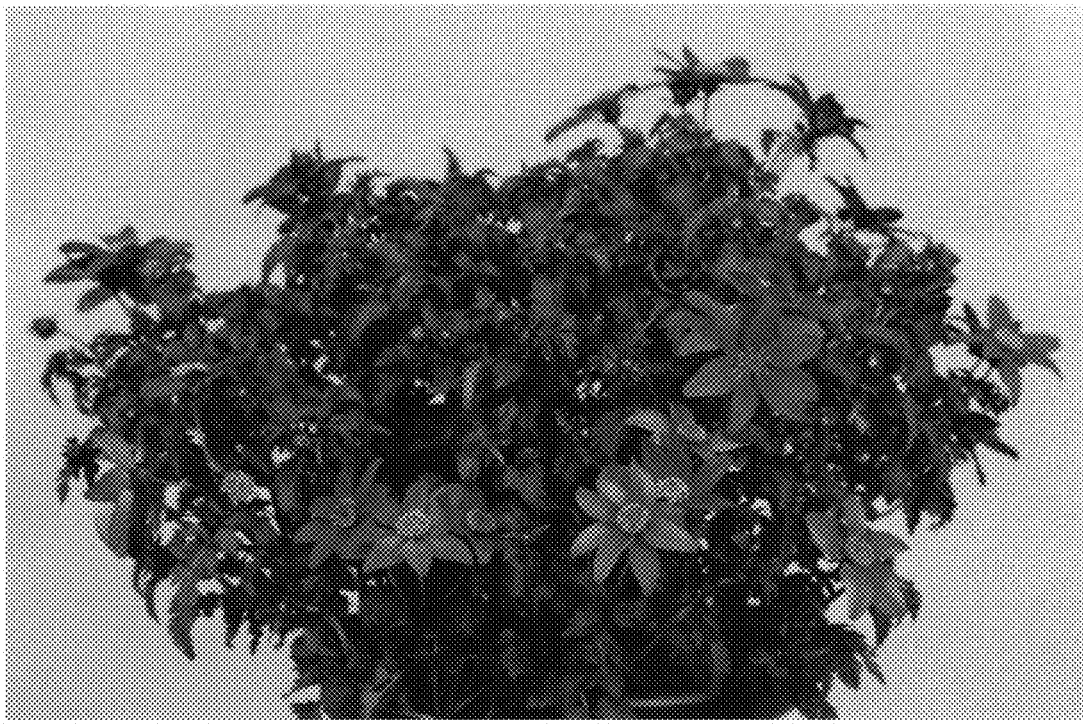
Figure 2:
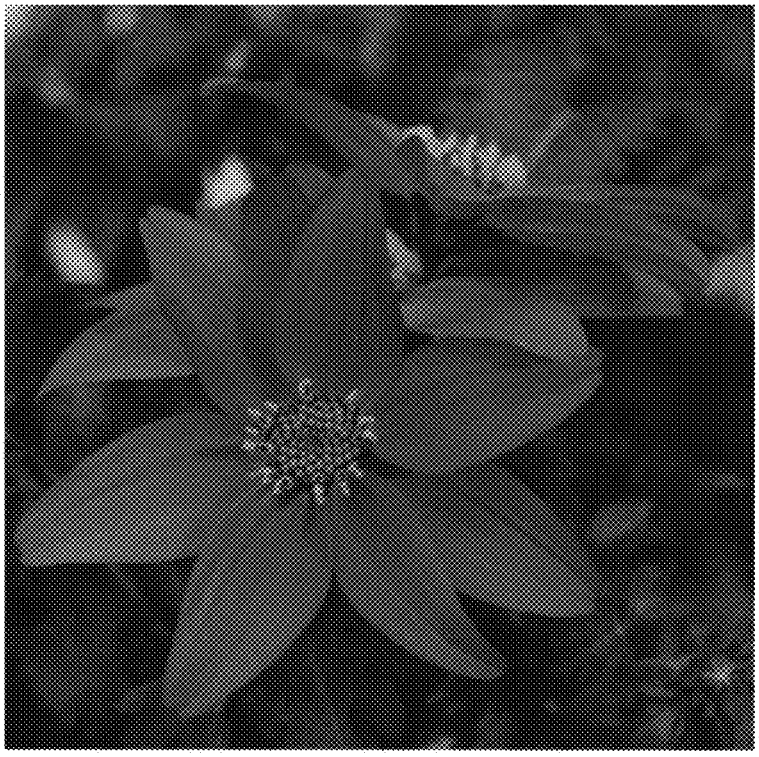

The photograph in FIG. 2 provides a close-up view of the inflorescenses of '15S27'.

Figure 3:
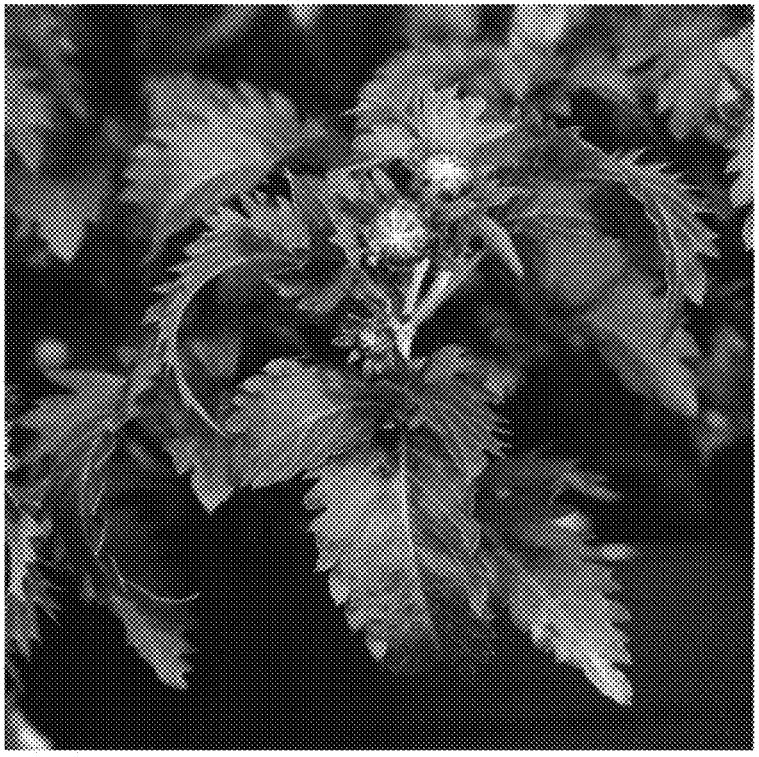

The photograph in FIG. 3 provides a close-up view of the foliage of '15S27'.

The colors in the photographs are as close as possible with the photographic and printing technology utilized and the color values cited in the detailed botanical description accurately describe the colors of the new *Bidens*.

DETAILED BOTANICAL DESCRIPTION

The following is a detailed description of 3 month-old plants of '15S27' as grown in 13-cm containers in an unheated greenhouse in Boskoop, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—Blooms from late May until November in Boskoop, The Netherlands.

*Plant type.*—Herbaceous perennial.

*Plant habit.*—Clump-forming, compact, broadly spreading, upright leafy flowering stems with inflorescences held above the foliage.

*Height and spread.*—An average of 11.9 cm (from soil level to uppermost stem leaf), 14.4 cm (from soil level to top of inflorescences), 33.6 cm in width as a 3-month old plant as grown in a 13-cm container.

*Cold hardiness.*—At least to U.S.D.A Zones 9 to 11.

*Diseases and pests.*—No susceptibility and resistance to pests and diseases has been observed.

*Root description.*—Fibrous and fine.

*Propagation.*—Stem cuttings.

*Root development.*—About 2 weeks to initiation roots and 3 weeks to root as a young plant as a liner in summer.

*Growth rate.*—Moderate.

Stem description:

*Shape.*—Rounded, very slightly angled.

*Stem color.*—Young, 146D, mature 166A.

*Stem size.*—An average of 12.5 cm in length and 2 mm in diameter.

*Stem surface.*—Slightly glossy, stems densely covered with short soft hairs, average of 0.8 mm in length, very minute in size, too small to measure length or color.

*Stem strength.*—Strong.

*Stem aspect.*—Held at an average angle of 45°.

*Branching habit.*—Lateral branches grow from a single main stem, an average of 9 lateral branches, an average of 1 main branch.

*Internode length.*—An average of 1.6 cm.

Foliage description:

*Leaf division.*—Single.

*Leaf arrangement.*—Opposite.

*Leaf attachment.*—Petiolate.

*Leaf petioles.*—An average of 1.5 cm in length, 1.2 mm in diameter, medium strength, upper surface; 177B in color, slightly glossy and moderately covered with short soft hairs, average of 0.75 mm in length, very minute in size, but closest to NN155D in color, lower surface; 145A in color, slightly glossy and glabrous.

*Leaf shape.*—Whole leaf and leaflet; ovate.

*Leaf quantity.*—Whole leaf; 12 per lateral branch, lobes; 3 per whole leaf.

*Leaf margins.*—Whole leaf deeply incised and lobes; crenate-serrate.

*Leaf lobes.*—Terminal lobe occasionally lobed, medium to deep sinuses, convergent orientation.

*Leaf size.*—Whole leaf; An average of 3.9 cm in length and 3.3 cm in width, side lobes; 1.8 cm in length and 1.3 cm in width, terminal lobe 3.1 cm in length, and 1.8 cm in width.

*Leaf base.*—Attenuate.

*Leaf apex.*—Acute.

*Leaf venation.*—Whole leaf and lobes; pinnate, upper surface 144B, tinged with 165A, lower surface 138B.

*Leaf surface.*—Upper and lower surface smooth, glabrous.

*Leaf color.*—Young upper surface 137B, young lower surface 138A to 138B, mature upper surface between 137A and 137B, mature lower surface 138B.

Flower description:

*Inflorescence type.*—Terminal and axillary capitulums, upright.

*Lastingness of inflorescence.*—Average of 2 weeks, discs persistent, ray florets self-cleaning.

*Fragrance.*—Faint sweet scent.

*Quantity of inflorescences.*—Free flowering, with an average of 90 inflorescences per plant.

*Inflorescence size.*—An average of 1.4 cm in height, 4.8 cm in diameter.

*Inflorescence buds.*—Ovate in shape, an average of 1.2 cm in depth and 8 mm in diameter (excluding the involucral bracts), smooth and glossy surface, color; 137C, immature ray florets 165A.

*Peduncle.*—Rounded in shape, strong, 138B in color, surface is matte and sparsely pubescent covered with short soft hairs, average of 0.1 mm in length, very minute in size, too small to measure color, terminal peduncle; 3.3 cm in length, 1 mm in diameter, held straight vertical, third peduncle; 4.2 cm in length, 1 mm in diameter, held in an average angle of 20° to the axis.

Involucral bracts:

*Involucral number.*—Two rows of 14.

*Involucral arrangement.*—Spirally placed around involucrum.

*Involucral size.*—An average of 7 mm in length, 1.5 mm in width.

*Involucral color.*—Fully open upper surface outer (lower row) 137B, fully open upper surface inner (upper row) between 197A and N199A, fully open lower surface outer (lower row) 137C, fully open lower surface inner (upper row) 197A.

*Involucral texture.*—Upper surface glabrous and smooth, lower surface moderately pubescent with short soft hairs, average of 0.5 mm in length, very minute in size, but closest to NN155D in color.

*Involucral apex.*—Acute.

*Involucral base.*—Broad cuneate.

*Involucral shape.*—Lanceolate.

Ray florets (no reproductive organs):

*Number.*—7, an average of 2 rows (whorls).

*Shape.*—Slightly carinate, rotate around disc.

*Size.*—An average of 2.4 cm in length and 1.7 cm in width.

*Apex.*—Praemorse.

*Base.*—Short attenuate.

*Margins.*—Entire, undulation is low.

*Aspect.*—Nearly horizontal to slightly upward, an average angle of 5° to horizontal.

*Texture.*—Upper surface; glabrous, matte, smooth and velvety, lower surface; glabrous, matte, smooth and very slightly velvety.

*Color.*—When opening upper surface between 178B and 180A, fading to 163A and 163B at the base, when opening lower surface N170A to N170B, fading to 163B to 163C at the base, when fully open upper surface 179A, lower half 163A, when fully open lower surface 164A, fading to 162A at the base.

Disc florets:

*Number.*—An average of 70, average of 7 rows (whorls).

*Shape.*—Tubular, lower 91% fused into tube, free tips.

*Aspect.*—Upright.

*Size.*—Average of 1.1 cm in length and 1.25 mm in width.

*Apex.*—Acute.

*Margins.*—Entire.

*Base.*—Fused into a tube.

*Texture.*—Upper surface moderately glossy, lower surface glossy, both surfaces smooth and glabrous.

*Color.*—Upper and lower surface when opening and fully open; 15A, upper and lower surfae when fully open; base 150C, mid-section to tip 13B.

*Receptacle.*—An average of 1 mm in depth, 4 mm in width, 145C in color.

*Receptacle spines.*—A single receptacle spine is placed next to each individual disc floret, acicular in shape, 7 mm in length, 0.8 mm in diameter, acute apex, cuneate base, smooth and glabrous surfaces, color; apex 200A, mid-section and base 145C to 145D.

Reproductive organs:

*Presence.*—Disc florets only.

*Gynoecium.*—1 Pistil, an average of 6 mm in length, stigma; decurrent, reflexed, 0.8 mm in length, 1.5 mm in diameter, 17B in color, style; 5.2 mm, 154C to 154D in color, ovary; 145C in color.

*Androecium.*—5 stamens, anther; basifixed, linear, 2 mm in length, 0.3 mm in width, 200A in color, filament; 3 mm in length, 150C to 150D in color, pollen; low in quantity, 23A in color.

*Seed.*—No seed development was observed to date.

It is claimed:

1. A new and distinct cultivar of *Bidens* plant named '15S27' as herein illustrated and described.

* * * * *